United States Patent
Lee (12)

(10) Patent No.: US 6,176,844 B1
(45) Date of Patent: Jan. 23, 2001

(54) CATHETER SYSTEM FOR THE ISOLATION OF A SEGMENT OF BLOOD VESSEL

(76) Inventor: Peter Y. Lee, 5118 Beechgrove NE., Canton, OH (US) 44705

(*) Notice: Under 35 U.S.C. 154(b), the term of this patent shall be extended for 0 days.

(21) Appl. No.: 09/080,581

(22) Filed: May 18, 1998

Related U.S. Application Data

(60) Provisional application No. 60/047,429, filed on May 22, 1997.

(51) Int. Cl.[7] .................................................. A61M 29/00
(52) U.S. Cl. .................................... 604/101.04; 604/99.01
(58) Field of Search ............................. 604/96, 101, 164, 604/167, 169, 256, 280, 523, 528, 96.01, 97.01, 98.01, 99.01, 99.02, 99.04, 101.01, 101.04, 101.05, 103.04, 164.01–164.03, 164.13, 167.01, 167.02, 915, 917, 919; 606/192, 194, 195

(56) References Cited

U.S. PATENT DOCUMENTS

| | | | |
|---|---|---|---|
| 4,921,483 | * | 5/1990 | Wijay et al. .......................... 604/96 |
| 5,158,540 | * | 10/1992 | Wijay et al. .......................... 604/43 |
| 5,906,606 | * | 5/1999 | Chee et al. .......................... 604/527 |
| 5,913,842 | * | 6/1999 | Boyd et al. .......................... 604/28 |
| 5,925,016 | * | 7/1999 | Chornenky et al. .................. 604/96 |
| 5,954,694 | * | 9/1999 | Sunseri .................................. 604/96 |

OTHER PUBLICATIONS

J. G. Webb, et al., "An Emboli Containment System for Saphenous Vein Graft Angioplasty," Transcatheter Therapeutic Conference, Washington, D.C. (Oct. 1998).

* cited by examiner

Primary Examiner—Wynn Wood Coggins
Assistant Examiner—LoAn H. Thanh
(74) Attorney, Agent, or Firm—Fay, Sharpe, Fagan, Minnich & McKee, LLP

(57) ABSTRACT

A catheter for isolating a segment of blood vessel has a guiding catheter (10) with proximal and distal ends. The guiding catheter (10) has major and minor lumens (12, 14). A first balloon (16) is attached to the guiding catheter (10) at the distal end thereof. The first balloon (16) is connected via the minor lumen (14) to a first inflation port (18) such that as fluid is injected into the first inflation port (18) the first balloon (16) expands. A proximal assembly (20) connected to the major lumen (12) at the proximal end of the guiding catheter (10) has an aspiration port (24) for evacuating the major lumen (12). A guidewire (30) extending through the major lumen includes a hollow tube (32) having proximal and distal ends. A wire (34) with a shapeable core is attached to the distal end of the hollow tube (32) forming a seal therewith. A plug (52) is selectively inserted into the proximal end of the hollow tube (32) forming a seal therewith. A second balloon (36) is attached to the distal end of the hollow tube (32) such that the second balloon (36) is expanded as fluid is received therein from a hole (38) in the hollow tube (32). A detachable manifold (40) holds the proximal end of the hollow tube (32) and the plug (52) in alignment with one another. The manifold (40) has a second inflation port (46) through which fluid is injected into the hollow tube (32) thereby expanding the second balloon (36).

16 Claims, 4 Drawing Sheets

CATHETER SYSTEM FOR THE ISOLATION OF A SEGMENT OF BLOOD VESSEL

This application claims the benefit of U.S. Provisional Application Ser. No. 60/047,429, filed May 22, 1997.

BACKGROUND OF THE INVENTION

The present invention relates to the art of transcatheter interventional procedures. It finds particular application in conjunction with thrombectomies, and will be described with particular reference thereto. However, it is to be appreciated that the present invention is also amenable to other analogous applications where isolation of a segment of a blood vessel or other tubular organ is desired.

Generally, catheters are well known in the medical arts. In the course of transcatheter interventional procedures, it is often desirable to isolate a segment of a blood vessel or other tubular organs temporarily. This allows for localized infusion of medications and treatment. Moreover, with different medical procedures, often various equipment, tools, and/or instruments are employed such that repeated access to a diseased site is desirable. In the past, catheter systems lacked these features.

In the case of blood vessels, a thrombectomy often involves the maceration of a thrombus and removal of debris. However, in previous procedures there existed the risk of embolization of the debris.

In one type of thrombectomy, the Folgerty-type, a Folgerty balloon is passed beyond the thrombus, inflated, and then pulled back while still inflated. This pulls the thrombus out with the balloon. However, the drawback to this technique is that it is relatively invasive and destructive. That is to say, typically, an arteriotomy is performed through which the Folgerty balloon is pulled to remove the thrombus. Generally, minimally invasive procedures are preferred.

With peripheral vascular grafts, such as those in the legs, often the graft is either a vein or Teflon. After time, a clot may form in the graft up to, in some cases, ten inches long. Commonly, such a clot is opened up by dripping a thrombolytic drug onto the clot. However, this technique is lengthy and requires that a catheter remain inserted, in some cases, up to 24 to 48 hours. Generally, relatively long procedures are undesirable where they may be avoided.

The present invention contemplates a new and improved catheter system and technique for the isolation of a segment of a blood vessel or other tubular organ which overcomes the above-referenced problems and others.

SUMMARY OF THE INVENTION

In accordance with one aspect of the present invention, a catheter for isolating a segment of a blood vessel is provided. It includes a guiding catheter having a proximal end and a distal end. The guiding catheter has a major lumen and minor lumen arranged in parallel. A first expandable latex balloon is attached circumferentially to an outside of the guiding catheter at the distal end thereof. The first expandable latex balloon is connected via the minor lumen to a first inflation port arranged at the proximal end of the guiding catheter. Fluid injected through the first inflation port expands the first expandable latex balloon. A proximal assembly is connected to the major lumen at the proximal end of the guiding catheter. The proximal assembly includes an aspiration port coupled to the major lumen for evacuating material from the major lumen. A guidewire extends through the major lumen. The guidewire includes a hollow tube having a proximal end and a distal end. A solid segment of wire with a shapable core is attached to the distal end of the hollow tube forming a seal therewith. A plug is selectively inserted into the proximal end of the hollow tube to form a seal therewith. A second expandable latex balloon is circumferentially attached to the distal end of the hollow tube such that the second expandable latex balloon expands as fluid is received therein from a hole in the hollow tube. A detachable manifold holds the proximal end of the hollow tube and the plug in alignment with one another when the plug is not inserted into the proximal end of the hollow tube. The detachable manifold includes a second inflation port through which fluid is injected into the hollow tube thereby expanding the second expandable latex balloon.

In accordance with another aspect of the present invention, a catheter system for isolating a segment of a tubular organ is provided. It includes a guiding catheter having proximal and distal ends. The guiding catheter includes a major lumen and a first balloon that is selectively expandable. The first balloon is attached to the outside of the guiding catheter at the distal end thereof. A guidewire extends through the major lumen. The guidewire includes a hollow tube having proximal and distal ends. A second balloon that is selectively expandable is attached to the hollow tube at the distal end thereof. A plug is selectively joined with the proximal end of the hollow tube forming a seal therewith. A manifold holds the proximal end of the hollow tube and the plug in alignment with one another when the plug is not joined with the proximal end of the hollow tube.

In accordance with a more limited aspect of the present invention, the manifold is independently detachable from the proximal end of the hollow tube and the plug.

In accordance with a more limited aspect of the present invention, the manifold further includes fittings that hold the proximal end of the hollow tube and the plug. The fittings are independently adjustable for selectively forming seals around the proximal end of the hollow tube and around the plug.

In accordance with a more limited aspect of the present invention, the second balloon is circumferentially attached to the distal end of the hollow tube and is coupled thereto via a hole in a side of the hollow tube.

In accordance with a more limited aspect of the present invention, the manifold further includes an inflation port which is coupled to the hollow tube when the manifold holds the proximal end of the hollow tube and the plug is not joined therewith. Pressure applied through the inflation port expands the second balloon.

In accordance with a more limited aspect of the present invention, the plug is joined with the proximal end of the hollow tube to maintain the pressure applied to the second balloon such that the second balloon remains expanded after the manifold is detached from the proximal end of the hollow tube and the plug.

In accordance with a more limited aspect of the present invention, the guiding catheter further includes an aspiration port arranged at the proximal end of the guiding catheter. The aspiration port is coupled to the major lumen for evacuation of material therefrom.

In accordance with a more limited aspect of the present invention, the guiding catheter further includes a minor lumen arranged in parallel with the major lumen. The minor lumen couples the first balloon to an inflation port arranged at the proximal end of the guiding catheter such that pressure applied through the inflation port expands the first balloon.

In accordance with a more limited aspect of the present invention, the guiding catheter further includes a fitting arranged at the proximal end of the guiding catheter. The fitting has the guidewire inserted therethrough. The fitting is independently adjustable for selectively forming a seal around the guidewire.

In accordance with another aspect of the present invention, a method for isolating a segment of a tubular organ is provided. The method includes inserting a first end of a guide tube through a wall of the tubular organ. The first end of the guide tube is positioned at a first end of the segment being isolated. A first end of a guidewire is passed through the guide tube and positioned at a second end of the segment being isolated opposite the first end of the segment being isolated. An outer diameter of the first end of the guide tube is expanded until it forms a seal with the wall of the tubular organ. An outer diameter of the first end of the guidewire is expanded until it forms a seal with the wall of the tubular organ.

In accordance with a more limited aspect of the present invention, the method further includes holding a second end of the guidewire opposite the first end of the guidewire with a manifold. Pressure is applied through the manifold to expand the outer diameter of the first end of the guidewire. The manifold is then detached from the second end of the guidewire.

In accordance with a more limited aspect of the present invention, a plug is held with the manifold such that the plug is spaced from, and in alignment with, the second end of the guidewire. After applying pressure, the plug is secured to the second end of the guidewire to maintain the applied pressure and keep the outer diameter of the first end of the guidewire expanded after the manifold is detached.

In accordance with a more limited aspect of the present invention, the method further includes coaxially threading ends of tools over the second end of the guidewire. The ends of the tools are extended down the guide tube and positioned in the segment of the tubular organ.

In accordance with a more limited aspect of the present invention, the method further includes conveying material via the guide tube from the segment of the tubular organ to outside the tubular organ.

In accordance with another aspect of the present invention, a catheter system for use in accessing a tubular organ is provided. It includes a guide catheter having a major lumen and a first selectively expandable balloon. The first selectively expandable balloon is attached at a first end of the guide catheter. A guidewire extends through the major lumen such that a first end of the guidewire projects out the first end of the guide catheter. The guidewire includes a second selectively expandable balloon attached to the first end of the guidewire.

In accordance with a more limited aspect of the present invention, the catheter system further includes a manifold for selectively inflating the second selectively expandable balloon. The manifold connects to a second end of the guidewire opposite that of the first end of the guidewire. The second end of the guidewire projects out a second end of the guide catheter opposite that of the first end of the guide catheter.

In accordance with a more limited aspect of the present invention, the manifold is selectively detachable.

In accordance with a more limited aspect of the present invention, the catheter system further includes selectively installable tools which are threaded over the guidewire when the manifold is detached such that they extend coaxially over the guidewire and through the guide catheter.

In accordance with a more limited aspect of the present invention, the first and second selectively expandable balloons are positioned within the tubular organ defining a segment of the tubular organ therebetween such that when the first and second selectively expandable balloons are expanded the segment of the tubular organ is isolated from a remaining portion of the tubular organ.

In accordance with a more limited aspect of the present invention, the tubular organ is a blood vessel.

One advantage of the present invention is its ability to isolate a segment of blood vessel or other tubular organ.

Another advantage of the present invention is that it protects against embolisms during thrombectomies and/or other treatments.

Another advantage of the present invention is that it permits repeated access with a number of various tools or instruments to a blood vessel or other tubular organ.

Another advantage of the present invention is its ability to deliver medication or treatment to an isolated region.

Another advantage of the present invention is the efficient and safe removal of a thrombus from a peripheral vascular graft.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
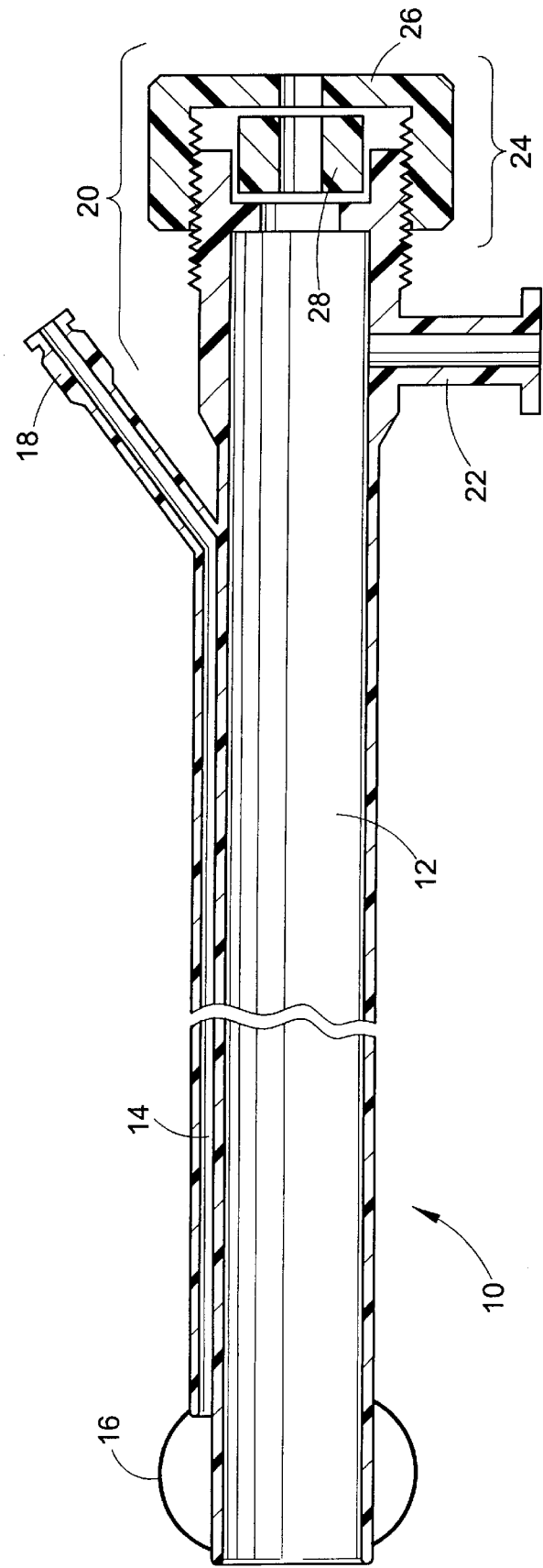
FIG. 1 is a diagrammatic illustration of a guiding catheter in accordance with aspects of the present invention.

With reference to FIG. 1, an introducer or guiding catheter 10 with proximal and distal ends has, extending along its length, a major lumen 12 and a minor lumen 14 arranged in parallel. An expandable balloon 16, preferably the latex-type, is attached circumferentially to an outside of the guiding catheter 10 at the distal end thereof. The expandable balloon 16 is connected via the minor lumen 14 to an inflation port 18 arranged at the proximal end of the guiding catheter 10. The inflation port 18 is a Luer Lock or other appropriate port. Fluid, such as a saline or heparinized saline solution, injected through the inflation port 18 is guided down the minor lumen 14 to the expandable balloon 16. The expandable balloon 16, in turn, stretches out and expands as it fills with fluid received from the minor lumen 14. When pressure at the inflation port 18 is released, the resiliency of the stretched out expandable balloon 16 causes it to collapse pushing fluid therein back out through the minor lumen 14. Optionally, for periphery applications, the balloon 16 is inflated with carbon dioxide.

A proximal assembly 20 is coupled to the major lumen 12 at the proximal end of the guiding catheter 10. The proximal assembly 20 has a side arm or aspiration port 22 open to the outside for evacuating the major lumen 12. A fitting 24 is attached to a terminal end of the proximal assembly 20. The fitting 24 is loosened and tightened to selectively open and close the terminal end of the proximal assembly 20 thereby selectively permitting insertion therethrough of desired tools and/or equipment. Moreover, when the fitting 24 is tighten with tools and/or equipment inserted therethrough a fluid tight seal is formed. In one optional configuration, the fitting includes a screw cap 26 and a washer 28, such as an o-ring or other appropriate sealing washer, arranged so that when the screw cap 26 is tightened an opening in the washer 28 constricts. Alternately, a sealing diaphragm having a variable aperture is employed. In any event, the mechanism employed is able to seal the major lumen 12 with variable diameter openings.

Figure 2:
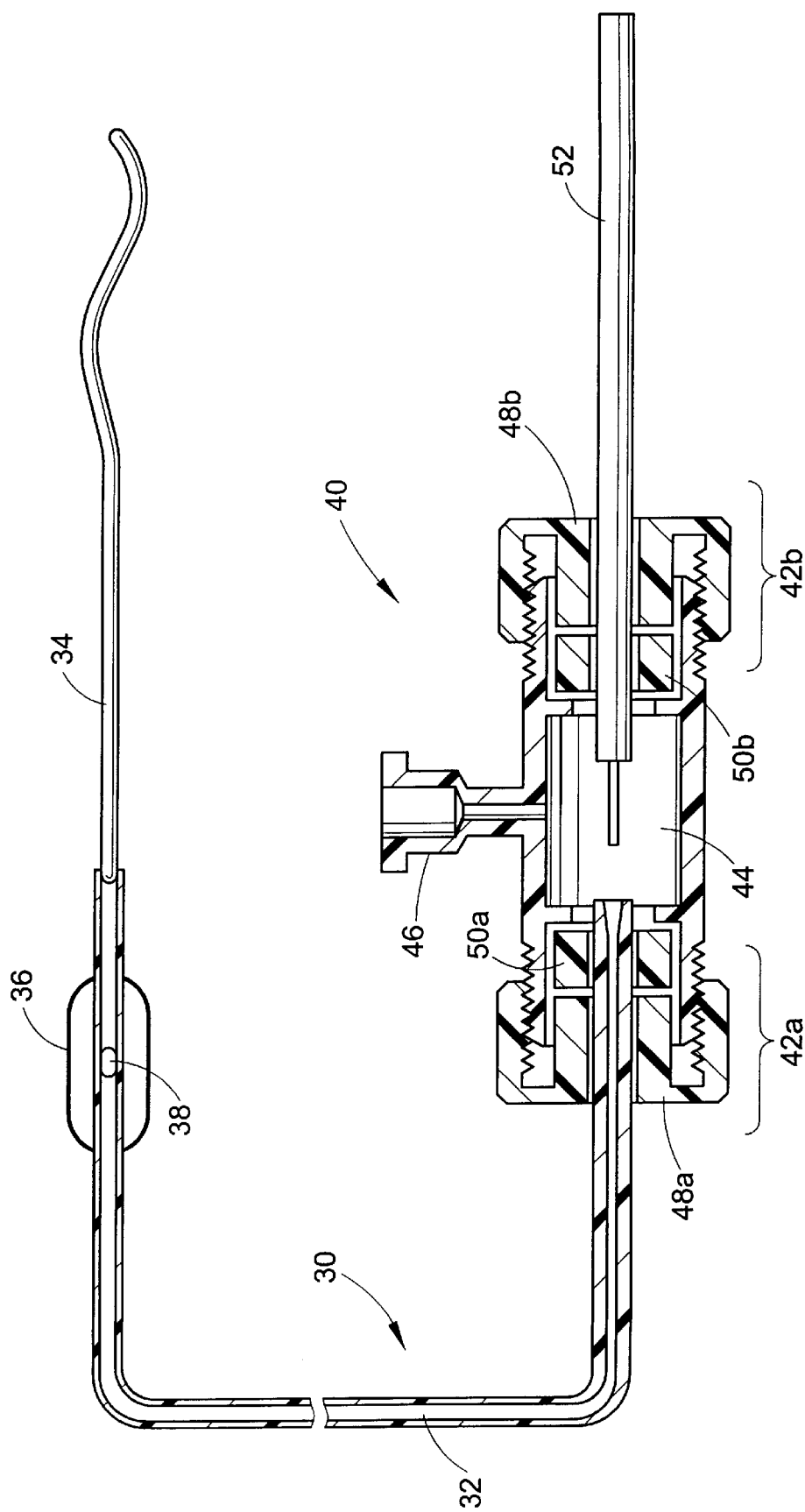
FIG. 2 is a diagrammatic illustration of a guidewire and manifold in accordance with aspects of the present invention.

With reference to FIG. 2, a guidewire 30 includes a hollow tube 32 having proximal and distal ends. The distal end is connected to a short segment of wire 34 with a shapeable core, such as those typically employed in an angioplasty guidewire. The distal end is therefore sealed. An expandable balloon 36, preferably the latex-type, is circumferentially attached to the distal end of the hollow tube 32. A hole 38 in a side of the hollow tube 32 at a distal end thereof is encompassed by the expandable balloon 36 and is used to inflate the balloon 36. The proximal end of the hollow tube 32 is held by a detachable manifold 40.

The manifold 40 includes two opposing fittings 42a and 42b connected by a hollow center portion 44 having a side arm or inflation port 46. In a preferred embodiment, the inflation port 46 is a Luer Lock or other appropriate port. Each of the opposing fittings 42a, 42b is loosened and/or tightened for selective opening and closing. Moreover, the fittings 42a, 42b form fluid seals when tighten around tools and/or equipment inserted therethrough or held therein. In one optional configuration, the fittings 42a, 42b include screw caps 48a, 48b and washers 50a, 50b, such as o-rings or other appropriate sealing washers, arranged so that when the screw caps 50a, 50b are tightened openings in the washers 48a, 48b constrict. Alternately, sealing diaphragms having variable apertures are employed. In any event, the mechanisms employed are able to seal the manifold 40 with variable diameter openings.

One of the fittings 42a has the proximal end of the hollow tube 32 inserted and held therein. The fitting 42a is tightened to achieve a fluid seal between the hollow tube 32 and the manifold 40. The opposing fitting 42b holds a plug 52 inserted therein in alignment with the proximal end of the hollow tube 32. The plug 52 and the hollow tube 32 have outer diameters or dimensions that are substantially the same. A fluid seal is also achieved between the plug 52 and the manifold 40. The side arm or inflation port 46 is used to inject fluid, such as a saline or heparinized saline solution, to inflate the expandable balloon 36 attached at the distal end of the hollow tube 32. Fluid injected through the inflation port 46 is guided down the hollow tube 32 to the expandable balloon 36. The expandable balloon 36, in turn, stretches out and expands as it fills with fluid received from the hole 38. When pressure at the inflation port 46 is released, the resiliency of the stretched out expandable balloon 36 causes it to collapse pushing fluid therein back out through the hole 38 and the hollow tube 32. Optionally, carbon dioxide is used to inflate the balloon 36 for peripheral applications.

With the balloon 36 inflated, the plug 52 is advanced into the proximal end of the hollow tube 32 to seal it and thereby maintain the inflation of the balloon 36. The fittings 42a, 42b are loosened and the manifold 40 detached by sliding it back over the plug 52. The assembly then becomes the plug 52 attached onto the proximal end of the hollow tube 32 to thereby cooperatively function as the guidewire 30 having continuously along its length the same outer diameter.

Figure 3A:
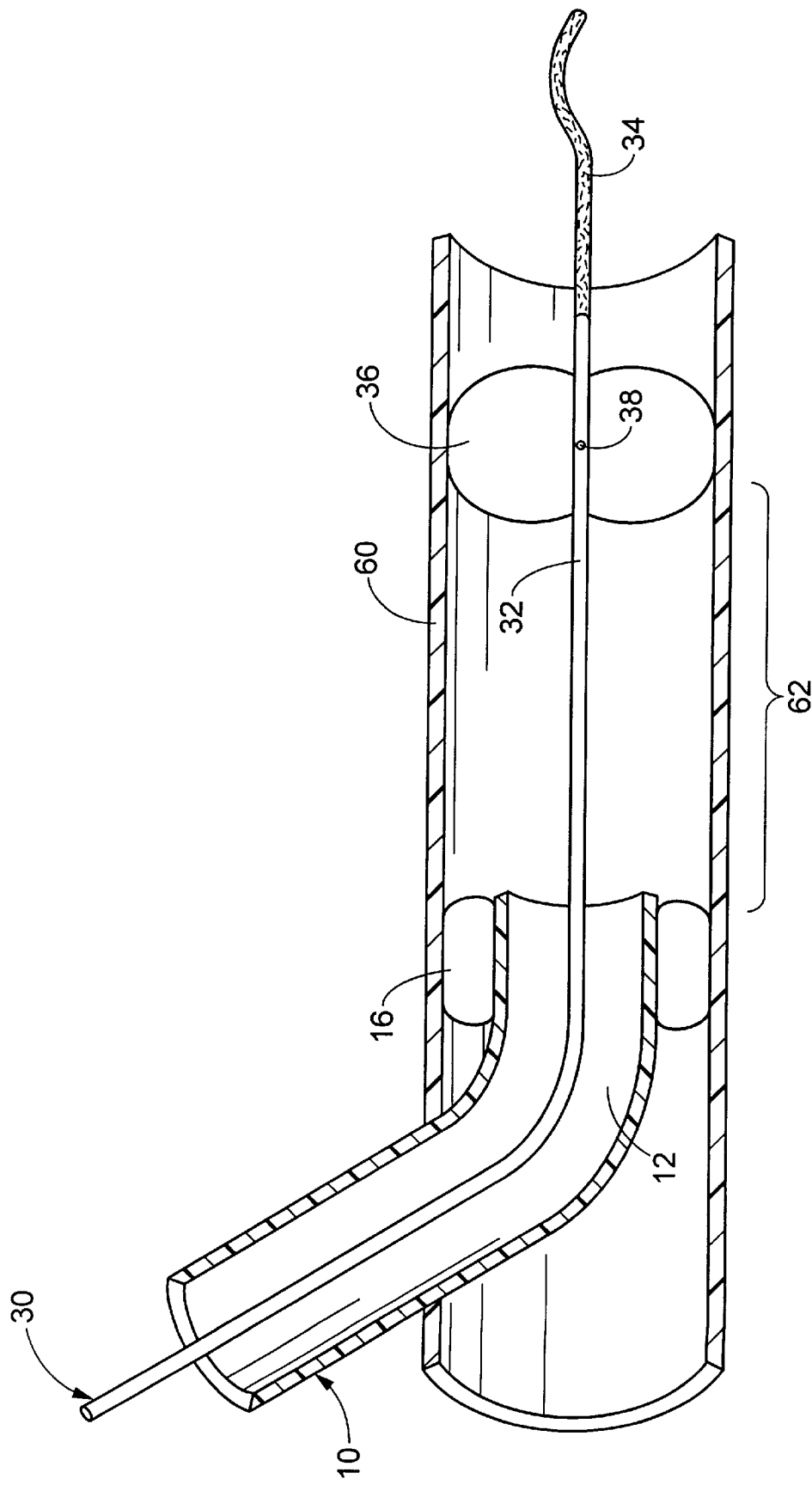
FIG. 3A is diagrammatic illustration showing the operation of a catheter system for the isolation of a segment of blood vessel in accordance with aspects of the present invention; and, FIG. 3B is a diagrammatic illustration showing the operation of a catheter system with an installed tool in accordance with aspects of the present invention.

With reference to FIG. 3A and continued reference to FIGS. 1 and 2, in operation, the proximal end of the guiding catheter 10 remains outside a subject's body while the distal end is inserted through a blood vessel wall 60 into the blood vessel and positioned so that the expandable balloon 16 is at one end of a segment 62 of the blood vessel that is to be isolated. Next, the guidewire 30 is installed by inserting the guidewire 30 through the fitting 24 of the proximal assembly 20 and extending it down the major lumen 12 of the guiding catheter 10 such that the expandable balloon 36 is positioned at an end of the segment 62 opposite from the expandable balloon 16. In this manner, the segment 62 of the blood vessel is isolated by inflating the balloons 16 and 36 until they are compressed against the blood vessel wall 60 forming seals therewith.

Alternately, the guidewire 30 is installed first. In this case, the guidewire 30 is inserted through the blood vessel wall 60 at a position just to one end of the segment 62 which is to be isolated. The guidewire 30 is extended the length of the segment 62 which is to be isolated such that the balloon 36 rests at an end opposite from that where the guidewire 30 was inserted. Next, the guiding catheter 10 is installed by threading it over the guidewire 30 and passing it through the blood vessel wall 62 at the same point where the guidewire 30 was inserted such that the balloon 16 rests at an end of the segment 62 which is to be isolated opposite that of balloon 36. Again, the segment 62 of the blood vessel is isolated by inflating the balloons 16 and 36 until they are compressed against the blood vessel wall 60 forming seals therewith.

In any event, the major lumen 12 ends as an opening at the distal end of the guiding catheter 10. Thus, a continuous space is created for flow between the blood vessel through the major lumen 12 of the guiding catheter 10 to the outside via the sidearm or aspiration port 22 of the proximal assembly 20. With the detachable manifold 40 removed, tools, such as irrigation catheters, interventional catheters, infusion catheters, and/or other desired equipment, are then co-axially passed over the guidewire 30 with installed plug 52, through the fitting 24 of the proximal assembly 20, and down the major lumen 12 of the guiding catheter 10 into the segment 62 of the blood vessel that is isolated. With the manifold 40 detached, repeated access and change of tools is achieved by sliding the installed tool back out over the guidewire 30 with attached plug 52 and co-axially installing the next tool. Optionally, multiple tools are co-axially installed. The first is threaded over the guidewire 30 and, via the fitting 24, through the major lumen 12; the second is threaded over the first in the same manner; and so on, until all the desired tools are installed.

Figure 3B:
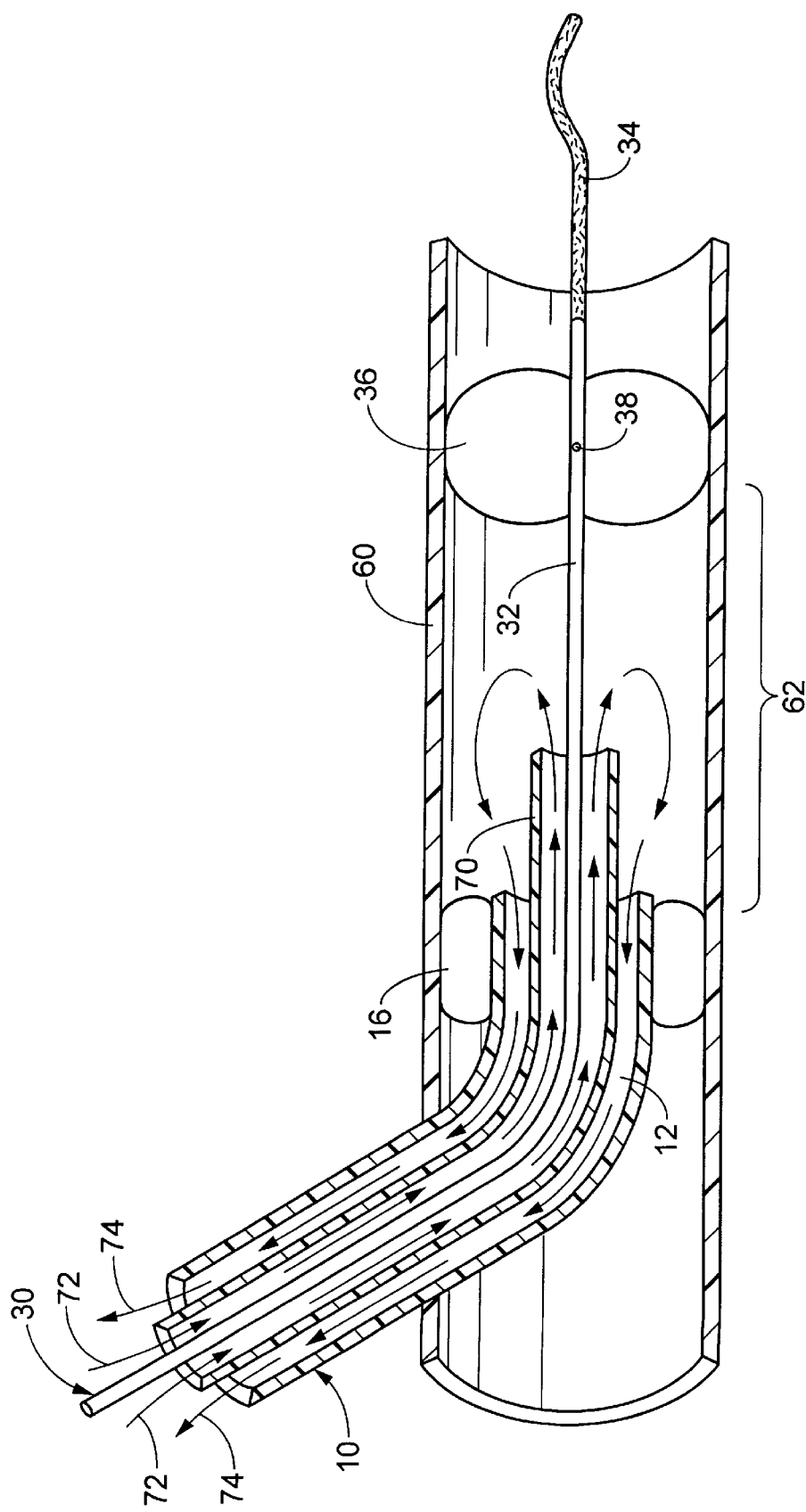

With reference to FIG. 3B, in a preferred embodiment, a tool (e.g., an infusion catheter 70) is shown installed with the end of the tool positioned in the isolated segment 62 of the blood vessel. The installed catheter 70 is used for infusion while the guiding catheter 10 is used for aspiration thereby removing debris from the isolated segment 62 of the blood vessel. More specifically, the installed catheter 70 injects infusates 72 or saline under high pressure to erode or otherwise macerate a thrombus in the isolated segment 62 of the blood vessel. The isolated segment 62 of the blood vessel is rinsed out having aspirates 74, waste, and/or debris from the macerated thrombus being removed via the major lumen 12 and aspiration port 22. Optionally, the procedure works in reverse with the guiding catheter 10 employed for infusion and the installed catheter 70 employed for aspiration. In either case, this technique is particularly useful in a thrombosed arterial bypass graft where a large amount of material is expected. Moreover, this allows extraction of the material without significant risk of embolization.

In another preferred application, a Folgerty-type procedure is performed with the balloon 36 acting as the Folgerty balloon. With the balloon 36 inflated, the guidewire 30 is extracted through the guiding catheter 10. This pulls a thrombus located in the isolated segment 62 of the blood vessel into the guiding catheter 10 ahead of the balloon 36 thereby clearing the blockage and trapping it in the guiding catheter 10. Optionally, an installed tool having a third balloon employed as the Folgerty balloon is used to clear the thrombus while the balloon 36 serves as a barrier to protect against embolization. Additionally, another tool installed behind the balloon being used as the Folgerty balloon (i.e. the third balloon or the balloon 36 depending on the procedure being performed) is used to macerate the thrombus prior to clearing by extraction of the inflated balloon.

While detailed above with particular reference to vascular catheters, the catheter system of the present invention is applicable to any tubular organ where isolation of a segment thereof is desired, where repeated access thereto with a number of various tools is desired, and/or where introduction of a medication to an isolated area is desired.

The invention has been described with reference to the preferred embodiments. Obviously, modifications and alterations will occur to others upon a reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A catheter for isolating a segment of a blood vessel comprising:
    a guiding catheter having a proximal end and a distal end, said guiding catheter including;
        a major lumen and a minor lumen arranged in parallel;
        a first expandable latex balloon attached circumferentially to an outside of the guiding catheter at the distal end thereof, wherein the first expandable latex balloon is connected via the minor lumen to a first inflation port arranged at the proximal end of the guiding catheter such that as fluid is injected through the first inflation port the first expandable latex balloon expands; and,
        a proximal assembly connected to the major lumen at the proximal end of the guiding catheter, the proximal assembly including:
            an aspiration port coupled to the major lumen for evacuating material from the major lumen;
    a guidewire which extends through the major lumen, said guidewire including;
        a hollow tube having a proximal end and a distal end;
        a solid segment of wire with a shapeable core attached to the distal end of the hollow tube forming a seal therewith; and,
        a plug which is selectively inserted into the proximal end of the hollow tube to form a seal therewith;
        a second expandable latex balloon circumferentially attached to the distal end of the hollow tube such that the second expandable latex balloon expands as fluid is received therein from a hole in the hollow tube; and,
    a detachable manifold which holds the proximal end of the hollow tube and the plug in alignment with one another when the plug is not inserted into the proximal end of the hollow tube, the detachable manifold including;
        a second inflation port through which fluid is injected into the hollow tube thereby expanding the second expandable latex balloon.

2. A catheter system for isolating a segment of a tubular organ comprising:
    a guiding catheter having proximal and distal ends, said guiding catheter including;
        a major lumen; and,
        a first balloon that is selectively expandable attached to an outside of the guiding catheter at the distal end thereof;
    a guidewire which extends through the major lumen, said guidewire including;
        a hollow tube having proximal and distal ends;
        a second balloon that is selectively expandable attached to the hollow tube at the distal end thereof; and,
        a plug that is selectively joined with the proximal end of the hollow tube forming a seal therewith; and,
    a manifold that holds the proximal end of the hollow tube and the plug in alignment with one another when the plug is not joined with the proximal end of the hollow tube.

3. The catheter system according to claim 2, wherein the manifold is independently detachable from the proximal end of the hollow tube and the plug.

4. The catheter system according to claim 3, wherein the manifold further includes:
    fittings that hold the proximal end of the hollow tube and the plug, which fittings are independently adjustable for selectively forming seals around the proximal end of the hollow tube and around the plug.

5. The catheter system according to claim 4, wherein the second balloon is circumferentially attached to the distal end of the hollow tube and it is coupled thereto via a hole in a side of the hollow tube.

6. The catheter system according to claim 5, wherein the manifold further includes:
    an inflation port which is coupled to the hollow tube when the manifold holds the proximal end of the hollow tube and the plug is not joined therewith, wherein pressure applied through the inflation port expands the second balloon.

7. The catheter system according to claim 6, wherein the plug is joined with the proximal end of the hollow tube to maintain the pressure applied to the second balloon such that the second balloon remains expanded after the manifold is detached from the proximal end of the hollow tube and the plug.

8. The catheter system according to claim 2, wherein the guiding catheter further includes:
    an aspiration port arranged at the proximal end of the guiding catheter, which aspiration port is coupled to the major lumen for evacuation of material therefrom.

9. The catheter system according to claim 8, wherein the guiding catheter further includes:
    a minor lumen arranged in parallel with the major lumen, which minor lumen couples the first balloon to an inflation port arranged at the proximal end of the guiding catheter such that pressure applied through the inflation port expands the first balloon.

10. The catheter system according to claim 9, wherein the guiding catheter further includes:

a fitting arranged at the proximal end of the guiding catheter, which fitting has the guidewire inserted therethrough, said fitting being independently adjustable for selectively forming a seal around the guidewire.

11. A method of isolating a segment of a tubular organ, said method comprising the steps of:

(a) inserting a first end of a guide tube through a wall of the tubular organ;

(b) positioning the first end of the guide tube at a first end of the segment being isolated;

(c) passing a first end of a guidewire through the guide tube;

(d) positioning the first end of the guidewire at a second end of the segment being isolated opposite the first end of the segment being isolated;

(e) expanding an outer diameter of the first end of the guide tube until it forms a seal with the wall of the tubular organ;

(f) applying pressure through a manifold which holds a second end of the guidewire opposite the first end of the guidewire to thereby expand an outer diameter of the first end of the guidewire until it forms a seal with the wall of the tubular organ; and, (g) detaching the manifold from the second end of the guidewire.

12. The method according to claim 11, further including:

holding a plug with the manifold such that the plug is spaced from and in alignment with the second end of the guidewire; and, after applying pressure, advancing the plug into the second end of the guidewire to maintain the applied pressure and keep the outer diameter of the first end of the guidewire expanded after the manifold is detached.

13. A catheter system for use in accessing a tubular organ, said catheter system comprising:

a guide catheter including:
a major lumen: and,
a first selectively expandable balloon attached at a first end of the guide catheter;

a guidewire which extends through the major lumen such that a first end of the guidewire projects out the first end of the guide catheter, said guidewire including:
a second selectively expandable balloon attached to the first end of the guidewire; and, a selectively detachable manifold for selectively inflating the second selectively expandable balloon, which manifold connects to a second end of the guidewire opposite that of the first end of the guidewire, wherein said second end of the guidewire projects out a second end of the guide catheter opposite that of the first end of the guide catheter.

14. The catheter system of claim 13, further comprising:

selectively installable tools which are threaded over the guidewire when the manifold is detached such that they extend co-axially over the guidewire and through the guide catheter.

15. The catheter system of claim 14, wherein the first and second selectively expandable balloons are positioned within the tubular organ defining a segment of the tubular organ therebetween such that when the first and second selectively expandable balloons are expanded the segment of the tubular organ is isolated from a remaining portion of the tubular organ.

16. The catheter system of claim 15, wherein the tubular organ is a blood vessel.

* * * * *